United States Patent [19]

Harris

[11] Patent Number: 5,096,808
[45] Date of Patent: * Mar. 17, 1992

[54] METHOD AND KIT FOR DETECTING HUMAN EXPOSURE TO GENOTOXIC AGENTS

[75] Inventor: Curtis C. Harris, Bethesda, Md.

[73] Assignee: The United States of America as represented by the Secretary of the Department of Health and Human Services, Washington, D.C.

[*] Notice: The portion of the term of this patent subsequent to Dec. 27, 2005 has been disclaimed.

[21] Appl. No.: 289,723

[22] Filed: Dec. 27, 1988

Related U.S. Application Data

[63] Continuation of Ser. No. 778,669, Sep. 23, 1985, Pat. No. 4,794,074.

[51] Int. Cl.$^5$ .................. C12Q 1/68; G01N 33/53
[52] U.S. Cl. .......................... 435/6; 436/501; 436/536; 436/813; 436/815; 436/64; 436/822; 435/7.1
[58] Field of Search .................. 435/6, 810, 7.1; 436/501, 536, 808, 809, 815, 813, 822, 64; 530/387

[56] References Cited

U.S. PATENT DOCUMENTS 4,172,117 10/1979 Schober .................. 424/1
4,444,879 4/1984 Foster et al. .................. 436/532
4,794,074 12/1988 Harris .................. 436/536

OTHER PUBLICATIONS

Poirier, M. C. Jour. Natl. Cancer Inst. 67:515-519 (1981).
Shamsuddin et al., Cancer Research 45:66-68 (1985).
Heine, W. I., et al., Journ. Amer. Med. Assoc. 182 No. 7:726-729 (1962).
Baird, W. M., Chemical Abstracts, vol. 89, No. 21, Abstract No. 174816y (1978).
Hsu et al., Cancer Res., 41:1091-1095 (1981).
Alarcon-Segovia, D., Mayo Clin. Proc. 44:664-681 (1969).
Dubroff, L., et al., Science 208:404-406 (1980).

Primary Examiner—Esther L. Kepplinger
Assistant Examiner—Toni R. Scheiner
Attorney, Agent, or Firm—Birch, Stewart, Kolasch & Birch

[57] ABSTRACT

The present invention discloses a method and a kit for monitoring human exposure to genotoxic agents. The method comprises an immunoassay for detecting in human serum specific antibodies against DNA adducted to an agent suspected of being genotoxic. A kit comprising various components for performing the assay is also disclosed.

2 Claims, 3 Drawing Sheets

METHOD AND KIT FOR DETECTING HUMAN EXPOSURE TO GENOTOXIC AGENTS

This is a continuation of application Ser. No. 778669 filed Sept. 23, 1985 now U.S. Pat. No. 4,794,074.

BACKGROUND OF THE INVENTION

1. Technical Field

The present invention is related to a method and a kit for detecting human exposure to genotoxic agents. More particularly, the present invention is related to immunoassays of antibodies to DNA adducted to a carcinogen or a mutagen, the presence of said antibodies in human serum being an indicator of human exposure to environmental carcinogens or mutagens and a kit containing various components for performing the assays.

2. State of the Art

Advanced technology and modern scientific development have produced several environmental pollutants, some being quite hazardous to health. Yet there are no objective means of monitoring human exposure to certain carcinogens or mutagens generally found in the industrial surroundings and in the atmosphere. The present invention provides an assay system and a kit for detecting the exposure of individuals to carcinogenic or mutagenic agents.

Of several hazardous elements prevailing in the atmosphere, benzo[a]pyrene (BP) is a ubiquitous chemical carcinogen found, for instance, in tobacco smoke, atmospheric pollution due to burning of fossil fuels, and a variety of foods (IARC Monographs on the Evaluation of the Carcinogenic Risk of Chemicals to Humans, 1983, World Health Organization, Lyon, Vol. 32, 211-224). In fact BP is so ubiquitous that it can be used as a reliable indicator of general exposure to other carcinogenic polycyclic aromatic hydrocarbons.

BP is a procarcinogen that requires metabolic activation, which results in its putative ultimate carcinogenic metabolite, $7\beta,8\alpha$-dihydroxy-$9\alpha,10\alpha$-epoxy-7,8, 9,10-tetrahydrobenzo[a]pyrene (BPDE) (Gelboin, *Physiol. Rev.* 60:1107-1166, 1980). The predominant DNA adducts formed from these compounds have been studied in experimental animals and in cultured human tissues and cells (Harris, et al., *J. Cell. Biochem.* 18:285-294, 1982; Jeffrey, et al., *Nature*, 269:348-350, 1977) and are found to be highly variable probably due to differences in metabolic enzymes.

DNA adduct levels are also dependent on DNA repair rates. Although rates for excision DNA repair vary several fold among people (Setlow, *Human Carconogenesis*, pp. 231-254, 1983), the interindividual variation in the DNA repair rates of these BPDE-DNA adducts in humans is not known. Therefore, the amount of adducts measured at any timepoint is dependent on many factors, including exposure to BP, its absorption and transport, the metabolic balance between activation and deactivation of BP and on the capacity of the cells to repair DNA adducts.

It should be noted that the methods of measuring DNA damage per se are known but heretofore it was not suspected that there might be antibodies present in human sera induced by DNA-carcinogen adducts and DNA damaged by oxidative stress caused by carcinogens (Cerutti. *Science* 227:375-281, 1985). Therefore, detection of antibodies in human sera to carcinogen-induced DNA damage, e.g., carcinogen-DNA adducts by immunoassays, was never thought of. As disclosed herein for the first time, the demonstration of the presence of antibodies to DNA-carcinogen adducts in human sera, provides an objective and reliable means to monitor human exposure to patho- biologically effective doses of chemical and physical carcinogens. This internal dosimeter of genetic damage reflected in terms of induced antibodies has unique advantages over merely measuring DNA damage directly in human cells.

First, the determination of just the DNA damage may reflect only the residual DNA damage, i.e., the DNA remaining after repair. Hence, such measurement may indicate only the present status of DNA damage, i.e., hours to days and this may only be an indicator of recent exposure to carcinogens. In contrast, the immunological memory found in lymphocytes, and the antibodies found in human sera could detect human exposure to carcinogens far into the past, i.e., years to decades. The finding of such antibodies in human sera was indeed unexpected because the intracellular DNA should normally remain protected from the immune systems, hence not normally expected to be available to form an antigenic entity.

SUMMARY OF INVENTION

It is, therefore, an object of the present invention to provide a method of detecting human exposure to genotoxic agents, such as carcinogens or mutagens.

It is a further object of the present invention to provide immunoassays for detecting in human serum the presence of antibodies to DNA adducts and oxidative DNA damage caused by chemical and physical agents as indicators of human exposure to carcinogens or mutagens.

It is a still further object of the present invention to provide a kit containing a plurality of components for performing the assays described herein.

Other objects and advantages will become apparent as the detailed description of the present invention proceeds.

BRIEF DESCRIPTION OF DRAWINGS

These and other objects, features and many of the attendant advantages of the invention will be better understood upon a reading of the following detailed description when considered in connection with the accompanying drawings wherein.

DETAILED DESCRIPTION OF INVENTION

Figure 1:
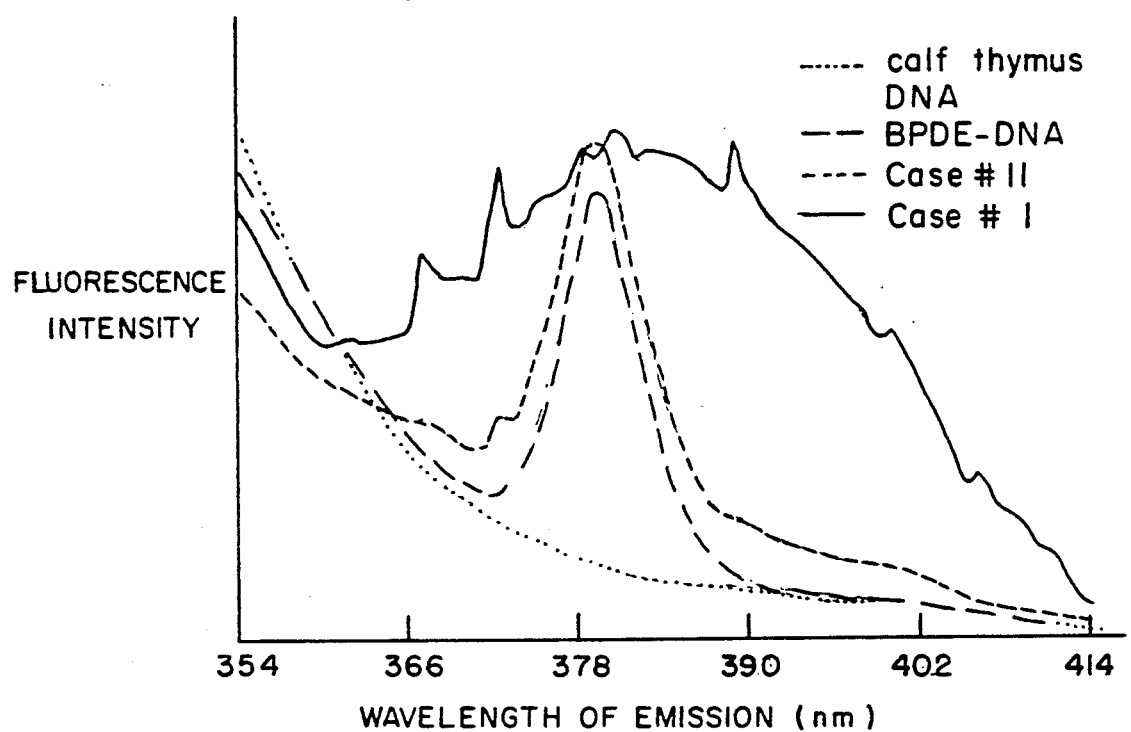
FIG. 1 shows SFS spectra of calf thymus DNA, BPDE-DNA, and peripheral blood lymphocyte DNA from two coke oven workers.

The above objects and advantages of the present invention are achieved by a kit and a method for detecting in human serum the presence of antibodies specific to DNA adducted to a genotoxic agent comprising: (a) plurality of containers each containing different DNA adducts of agents suspected of being genotoxic; (b) plurality of containers each containing different groups of antibodies, each group of antibodies being specific against a particular DNA adduct (c) microtiter plate; (d) micropipettes; (e) microtiter reader; (f) reagents for immunoassay; and (g) instructions for performing the assay. Of course, the antibodies can be either monoclonal, polyclonal or a mixture thereof.

The term "genotoxic agent" as used herein is defined to include both chemical and physical agents capable of causing damage to human DNA or the gene. Carcinogens and mutagens are common examples of chemical genotoxic agents, while UV radiation, γ and X-rays and the like when they produce oxidized DNA product are common examples of physical genotoxic agents.

Any carcinogen or mutagen which is capable of forming an adduct with DNA and/or causing oxidative damage to DNA can be monitored for its damaging effect on humans by employing the present assay. Various groups of chemicals known to form DNA adducts are exemplified in Table 1. Of course, the list appearing in Table 1 is non-limiting in scope and is only for illustrative purposes. In addition, physical agents such as ionizing radiation, ultraviolet light and the like are also known to cause DNA damage and adducts formed by thymine glycol, thymidine glycol, thymidine dimers and the like can also be utilized to monitor such damage in accordance with the present invention. (Table 1).

TABLE 1

CHEMICAL CARCINOGENS ACTIVATED TO FORM DNA ADDUCTS BY CULTURED HUMAN BRONCHUS, COLON, ESOPHAGUS, BLADDER AND PANCREATIC DUCT

| Carcinogen | Bronchus | Colon | Esophagus | Pancreatic Duct | Bladder |
|---|---|---|---|---|---|
| Polynuclear Aromatic Hydrocarbon | | | | | |
| Benzo[a]pyrene | + | + | + | + | + |
| 7,12-Dimethylbenza[a]anthracene | + | + | + | + | |
| 3-Methylcholanthrene | + | + | + | | |
| Dibenzia[h]anthracene | + | + | + | | |
| N-Nitrosamine | | | | | |
| Nitrosodimethylamine | + | + | + | + | |
| Nitrosodiethylamine | + | + | + | | |
| Nitrosopyrrolidine | + | + | — | | |
| Nitrosopiperidine | + | — | — | | |
| Dinitrosopiperazine | + | + | | | |
| Mycotoxin | | | | | |
| Aflatoxin B₁ | + | + | + | · | + |
| 1-2 Toxin | | | + | | |
| Hydrazine | + | + | + | | |
| 1,2-Dimethylhydrazine | | | | | |
| Aromatic Amine | | | | | |
| 2-Acetylaminofluorene | + | | + | · | + |
| Trp-P-1 (3-amino-1,4-dimethyl-5H-pyrido[4,3-b]indole) | | + | | | |

Although any similar or equivalent methods and materials can be used in the practice of the present invention or for the tests described herein, the preferred methods and materials are now described. All publications mentioned hereunder are incorporated herein by reference.

Certain preliminary essential steps for the practice of the present invention are as follows.

(a) Preparation of DNA adduct: Any carcinogen or mutagen, the human exposure to which is desired to be monitored or detected, and which will form an adduct with the human DNA can be used. Methods of preparing such mutagen-DNA or carcinogen-DNA adducts are well known in the art and can be found in such publication as Hsu et al., Cancer Res. 41:1091-1095 (1981).

(b) Obtaining antibodies to the adduct prepared in step (a): Preparation of such antibodies is necessary only if competition ELISA, vide infra, is utilized as an additional step. Any suitable animal can be used for obtaining the antibodies, e.g. goat, horse, rat, mouse, and the like. Methods of obtaining such antibodies are well known in the art and can be found in such publication as Haugen et al., Proc. Nat. Acad. Science USA 78:4124-4127 (1981).

Preferred embodiments illustrating the invention disclosed herein are now set forth. Since BP is the most ubiquitous carcinogen, the invention is being exemplified using BP as a model. Of course, the same procedure as used for BP can be employed for any other mutagen or carcinogen some of which have been listed in Table 1.

EXAMPLE—1

Donors

Because coke oven workers are exposed to substantial amounts of BP in their work atmosphere (7-10 $\mu g/m^3$) and are at increased risk of lung cancer (Redmond, et al., J. Occu. Med. 14:621-629, 1972), this occupational population was selected to determine if BDPDE-DNA adducts could be found in the DNA of their peripheral blood lymphocytes and if such products elicited an immune response and thus serum antibodies to these adducts.

Volunteer coke oven workers from a single plant were selected for the study. The mean age of the 41 participants was 45.0±9.6 years (mean±S.D.) and their ages ranged from 28 to 61 years. The minimum duration of work on the coke ovens was 5 years, and the maximum duration was 30 years. The mean number of years worked at the coke ovens was 17.8±4.2 years (mean±S.D.) and the median was 16.8 years. The participants were questioned about their smoking habits, work, diet, and medication using a standardized questionnaire administered by interview. Cigarette smoking was defined as consumption of more than 20 packs of cigarettes in a lifetime. Approximately 50 ml of blood was obtained from each of the 41 participants, and the uncentrifuged whole blood was shipped in plastic containers by an overnight express carrier to the National Cancer Institute, Bethesda, Md. for analysis. Work histories for the participants' employment at the coke ovens were available from the personnel office of the company. Industrial hygiene measurements of benzene-soluble particulates collected from the work area atmosphere for each coke oven job were also provided by the company. These measurements which were performed using methods specified by the OSHA standard for exposure to coke oven emissions (Federal Register, Vol. 41, No. 206, pp. 46742-46790, 1976), were used in the study to represent relative exposure to polycyclic aromatic hydrocarbons (PAH).

DNA (deoxyribonucleic acid) was purified from peripheral blood mononuclear cells which were frozen at −70° C. in HEPES (source, catalog #, full chemical name) buffer after isolation from peripheral blood using lymphocyte separation medium (Litton Bionetics, Rockville, Md). The cell suspension was thawed, diluted 1:1 with a buffer containing NaCl (100 mM), Tris (50 mM, pH 8.0), sodium dodecyl sulfate, SDS, (1%), and ethylenediaminotetracetic acid, EDTA, (10 mM), and the DNA isolated as described by Vahakangas et al. *Environ. Health Pers., in press* (1985). The serum for antibody studies from these individuals was frozen at −70° C. until used.

ELISA for Detection of Antibody to BDPDE-DNA Adducts

Non-competitive ELISA—Human serum samples were tested for the presence of antibodies against BDPDE-DNA by enzyme-linked immunosorbent assay (ELISA). The ELISA used is similar to the method of Hsu, et al., *Cancer Res.* 41:1091-1095 (1981). The BPDE-modified or unmodified DNA were used as the standard antigens. These were attached to polyvinyl-chloride microtiter plates (Costar, Cambridge, Mass.) by drying at 37° C. for 12 hr at the concentration of 20 ng/well in 50 $\mu$l of 20×SSC buffer (3M Nacl, 0.3M Sodium citrate, pH 7.0). Plates coated with the unmodified DNA or without DNA (SSC buffer alone) were used as controls. The plates without DNA were used to establish background binding levels of the test sera and the plates coated with unmodified DNA were used to distinguish antibodies that bound to DNA from those that bound to BPDE modified DNA. Plates were coated with BPDE-modified or unmodified bovine serum albumin by incubating 100 ng of these test antigens in 0.06M carbonate-bicarbonate buffer (pH 0.6) for 12 hr. These test agents were used to identify antibodies against BPDE alone. Affinity purified goat anti-human immunoglobulin reagents (Cappel Laboratories, West Chester, Pa.) were biotinylated as described by Warnke, et al., *J. Histochem. Cytochem.* 28:771-776 (1980) and stored at 1 mg/ml, 4° C.

Antigen-coated test plates were prepared for the assay by multiple washing steps using distilled water to remove salt crystals followed by a 30 min room temperature (23° C.-30° C.) incubation of all wells with 150 $\mu$l of a 0.05M phosphate-buffered saline containing 10% normal goat serum (PBS-NGS) to block protein binding sites on the solid phase. Human sera were tested in triplicate using 4 log$_5$ serial dilutions, with all dilutions being made in the PBS-NGS solution. Test sera (50 $\mu$/well) were incubated for about 60 with the antigen containing plates and then washed 5 times with PBS. The binding human immunoglobulin was detected using the biotinylated goat anti-human immunoglobulin reagents and the avidin-biotin horseradish-peroxidase system (ABC Vectastain kit, Vector Laboratories, Burlingame, Calif.) as described by the manufacturer. The enzyme reaction was developed by the addition of 100 $\mu$l of the substrate solution (0.5M citrate buffer, pH 4.0; 1 mg/ml orthophenylene-diamine; and 0.5 $\mu$/ml of 30% H$_2$O$_2$) to each of the wells. The enzymatic reaction was stopped after a 20 min room temperature (about 23°-30° C.) incubation by the addition of 50 $\mu$l of 2.0M H$_2$SO$_4$.

Plates were read using an automatic ELISA reader (Dynatech Laboratories, Alexandria, Va.) and the absorbance at 490 nm was recorded. An anti-human immunoglobulin reagent that reacted with all isotypes of human serum immunoglobulin was used for initial testing. Each ELISA included the testing of a serum on BP-modified and unmodified DNA as well as on a plate without any type of bound DNA. The modified and unmodified bovine serum albumin were used similarly.

Antigen Competition ELISA—Human sera that were found to contain antibodies that reacted against the BPDE-modified DNA were tested for specificity of reactions using a competitive ELISA. In this assay the binding of serum antibodies to solid phase antigen (BPDE-DNA) was competed by the preincubation of the sera with different test antigens (BPDE-modified- or unmodified-DNA) prior to testing in the ELISA. Human sera were diluted to a point at which binding was 80-90% maximal. The diluted sera were mixed with varying amounts of modified- or unmodified-DNA (400,200 and 100 ng/ml) and incubated at room temperature for 60 min. These serum-DNA mixtures were then tested as described for the noncompetitive ELISA against both the modified and unmodified DNA. The results were expressed as percent inhibition which was determined using the levels of binding of each serum without any competing antigen as the level of maximum binding and the background binding of each serum as the level of minimal antibody binding.

Assays for BPDE-DNA Adducts

A. Synchronous Fluorescence Spectrophotometry

The DNA solution was treated with 0.1M HCl and heated at 90° C. for 3 hours to hydrolyze the adducted DNA to putative BP tetrols as described by Vahakangas, et al., *Environ. Health Pers.*, in press (1985). The samples were assayed by a Perkin-Elmer fluorescence spectrophotometer 650-40 with Perkin-Elmer 3600 data station. All measurements were done using constant wavelength difference of 34 nm ($\lambda$34 nm) between excitation and emission during the scanning. By this system, the BPDE-DNA and hydrolysis products of BP tetraols given specific emission peaks at 382 and 379 nm consecutively Vahakangas, et al., *Environ. Health Pers.*, in press (1985).

B. Ultrasensitive Enzyme Radioimmunoassay (USERIA)

The USERIA as described by Harris, et al., *Proc. Natl. Acad. Sci. USA* 76:5336-5339 (1979) was employed to detect BPDE-DNA adducts. This assay method utilizes a rabbit antisera against BPDE-DNA and is performed in a manner similar to that described by Hsu, et al., *Cancer Res.* 41:1091-1095 (1981); Shamsuddin, et al., *Cancer Res.* 45:66-68 (1985). Polyvinyl microtiter plates are precoated with 0.2 ng of BPDE-DNA in 10×PBS (GIBCO) and stored at −20° C. Prior to adding the competition mixtures, the plates are washed free of salt and treated for 1 hr with 2% horse serum. For the test, 10 $\mu$g (or less) of each DNA sample is adjusted to 210 $\mu$l with buffer and heated to 90° C. for 15 minutes and then cooled in ice water to obtain single stranded DNA. An equal volume of 1:300,000 dilution of rabbit antiserum to BPDE-DNA in 2% horse serum is added to each sample and to tubes containing serially diluted BPDE-DNA prepared in 40 or 20 $\mu$g/ml solutions of unmodified DNA for the standard curve on each plate. One hundred $\mu$l of each antigen-antibody solution is added to a triplicate set of microtiter wells containing BPDE-DNA as the solid phase competitor and to one well containing unmodified DNA for the solid phase specificity control. The plates are incubated for about 90 minutes at 37° C. then washed, and alkaline phosphatase-conjugated goat anti-rabbit IgG (Fab

[Cappel] 1:500 in 1% horse serum) is added for an additional hour at 37° C. The plate is washed, and 100 μl of the substrate (20 pmoles tritiated paranitrophenyl phosphate [New England Nuclear, Boston, Mass.] and 80 pmoles of unlabelled substrate per well in 20 mM diethanolamine buffer (pH 9.6) containing 10 mM MgCl) is added, and the plate is incubated for about 4 hours at 37° C. Finally, 20 μl from each well is diluted in 2 ml of buffer and mixed with 4 ml of Econoflour 2 (Source, Chemical name, etc) separating hydrolysed tritiated paranitrophenol in the organic phase to measure the radioactivity for the final calculations of the inhibition of the immunoreactions when compared to the uninhibited controls.

The mean and standard deviation of each triplicate set are determined and the corrected means (minus control DNA values) are used to calculate the percent inhibition. The variation among triplicates is less than 20%. Cases judged as positive by USERIA produced a percent inhibition within the linear portion of the standard curve, i.e., between 20-25% and 80-85% inhibition.

BPDE-DNA Adducts

Synchronous Fluorescence Spectrophotometry (SFS)

Putative BPDE-DNA adducts are found as a peak at 378-380 nm of emission. Examples of emission spectra observed in testing DNA from 2 cases and comparison with a spectrum from BPDE modified calf thymus DNA are shown in FIG. 1. The 2 patterns exemplified in this figure are the sharp peak characteristic of the calf thymus DNA adduct and the broad peak. In most of the cases, the peaks were of the broad type rather than the sharp peak produced by hydrolysed authentic BPDE-DNA. Thirty-one out of 41 samples from different individuals show these patterns. The pattern in the 10 negative samples was similar to that seen with calf thymus DNA. SFS analysis is quantitative as well as qualitative. However, the broad peak does not allow specific quantitation. Hence, the results are expressed as either positive or negative.

USERIA

Sufficient DNA was available in only 27 of the 41 cases to measure BPDE-DNA adducts by USERIA. The standard curves were established with reference BPDE-DNA diluted in unmodified DNA (20 μg or 10 μg per microtiter will). The 50% inhibition ranged from 8 to 16 fmole and a minimum detectable level ranged from 0.06 to 0.23 fmole BPDE/μg DNA/well, i.e., a minimum detectability level of 1 mole BPDE in $2 \times 10^7$ moles of DNA.

Eighteen of the 27 samples tested (64%) were positive (Table 2), showing amounts that ranged from 0.4 to 34.3 fmole of BP/μg of DNA. Nonsmokers and exsmokers had approximately the same percentage of positives and no significant difference in the levels was detected. Smokers had a slightly higher proportion of positives (9/12, 75%) than nonsmokers and exsmokers combined (9/15, 60%). Among the cases in jobs with the highest exposure to benzene soluble particulates (Lorry car operator, door cleaner, lid tender, etc.), 6 of 7 caes (86%) were positive by USERIA.

Antibodies Towards BPDE-DNA

Sera from the same individuals whose lymphocyte DNA were studied for BPDE-DNA adducts were studied for antibodies to BPDE-modified DNA. Eleven of 41 (27% of the sera tested had patterns of reactions that suggested that these sera contain specific antibodies to BPDE-DNA (Table 2).

TABLE 2

Presence of Putative BPDE-DNA Adducts and Antibodies in Coke Oven Workers According to Tobacco Smoking History

| Sample # | Putative BPDE-DNA Adducts SFS[a] | USERIA[b] | Antibody Titer[c] |
|---|---|---|---|
| NEVER SMOKERS | | | |
| 3 | × | 1.2[d] | — |
| 7 | — | 4.3 | 625 |
| 9 | — | 1.1[d] | — |
| 24 | — | 1.4[d] | 25 |
| 26 | + | N.T.[e] | >3,125 |
| 35 | × | <0.06 | — |
| 37 | × | 4.4 | — |
| EXSMOKERS | | | |
| 1 | × | <0.06 | — |
| 2 | — | 0.9 | — |
| 5 | + | N.T. | — |
| 10 | × | 0.4 | — |
| 13 | — | 6.1 | — |
| 14 | + | N.T. | 125 |
| 16 | × | N.T. | — |
| 17 | + | N.T. | — |
| 19 | — | <0.06 | — |
| 21 | — | N.T. | — |
| 28 | × | <0.06 | >3,125 |
| 29 | × | <0.06 | — |
| 38 | × | 1.0 | — |
| 41 | — | <0.06 | — |
| CURRENT SMOKERS | | | |
| 4 | + | N.T. | — |
| 6 | — | <0.06 | — |
| 8 | — | N.T. | — |
| 11 | + | 26.5 | — |
| 12 | + | N.T. | — |
| 15 | × | <0.06 | — |
| 18 | × | N.T. | 125 |
| 20 | × | N.T. | — |
| 22 | × | 9.8 | — |
| 23 | × | 0.9 | — |
| 25 | + | 34.3 | 625 |
| 27 | × | 23.8 | — |
| 30 | × | 4.3 | >3,125 |
| 31 | × | <0.06 | — |
| 36 | + | N.T. | — |
| 39 | + | N.T. | — |
| 40 | × | N.T. | 625 |
| 42 | × | 2.7 | >3,125 |
| 43 | × | 2.3 | — |
| 44 | × | 2.0 | >3,125 |

Figure 2:
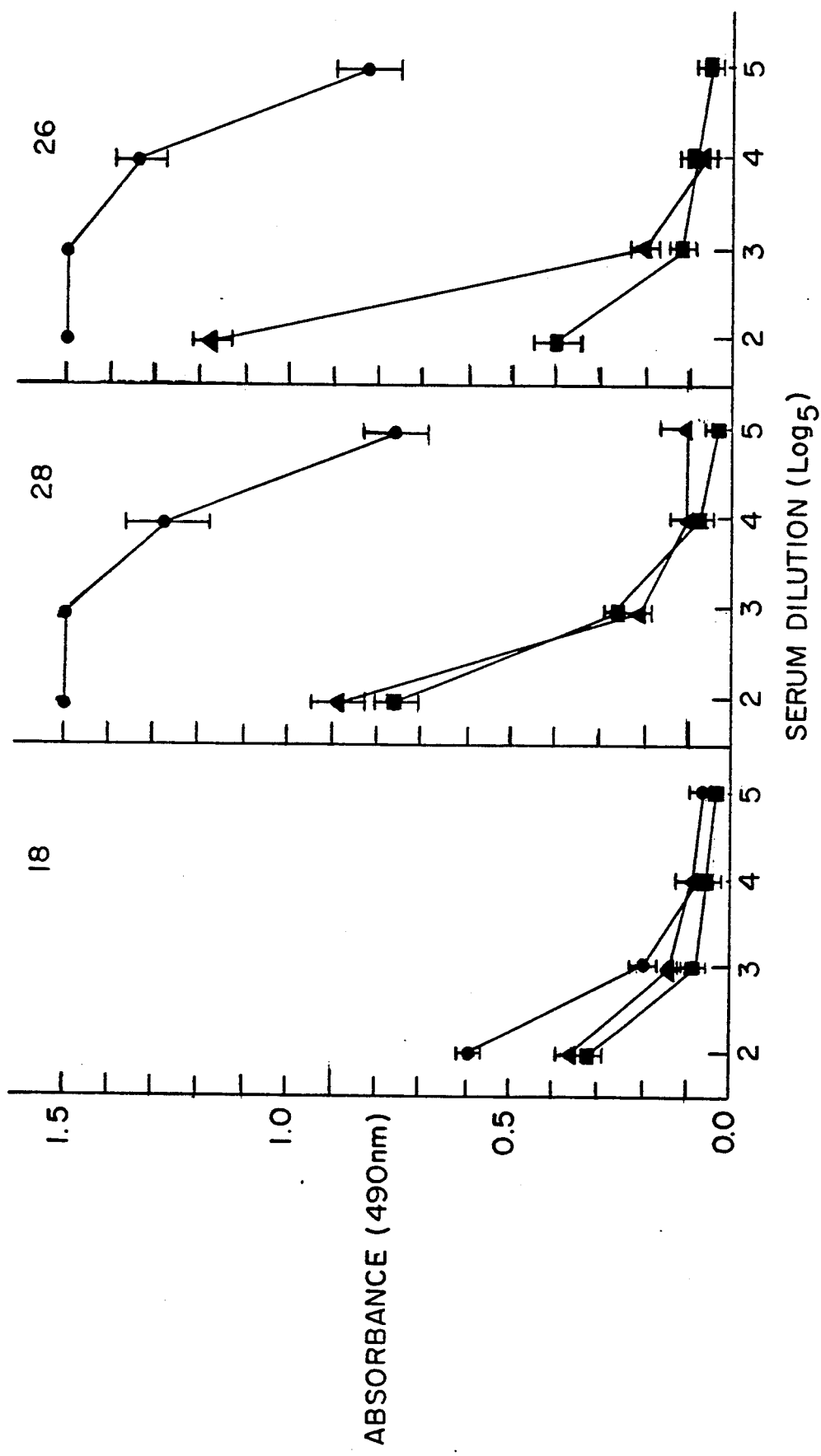
FIG. 2 shows binding curves of three human sera on BPDE-DNA ●——●, control DNA ▲——▲, and on no DNA plates ■——■. Data points represent the mean±(SEM) of triplicate noncompetitive ELISA absorbance values. The sera were tested using four $\log_{(5)}$ dilutions as described herein.

[a]Synchronous fluorescence spectrophotometry; +, sharp emission peak at 379 and 382 nm; ×, broad emission peak at 379 and 382 nm; and —, no peak at those wavelengths;
[b]fmoles per μg DNA
[c]When a number is not listed in the table, antibody to BPDE-DNA was not detected
[d]Mean; each assay was done in triplicate and the variation was generally less than 10%
[e]N.T., not tested; insufficient DNA remaining in unhydrolyzed aliquot after SFS to The ELISA binding curves established by dilution of the sera are of 3 types and are shown in FIG. 2: (a) 3 of the 11 positive sera produced antibody binding patterns similar to that shown for serum #18 in that the specific antibody titers to BPDE-DNA were low, i.e., 25-125, and no antibody reactivity to unmodified DNA was observed; (b) the binding patterns of 7 of 11 sera were similar to that shown for serum #28 and the titers were higher, i.e., 625 to ≧3125; and (c) the remaining positive serum, #26, reacted against both BPDE-DNA and unmodified DNA.

Figure 3:
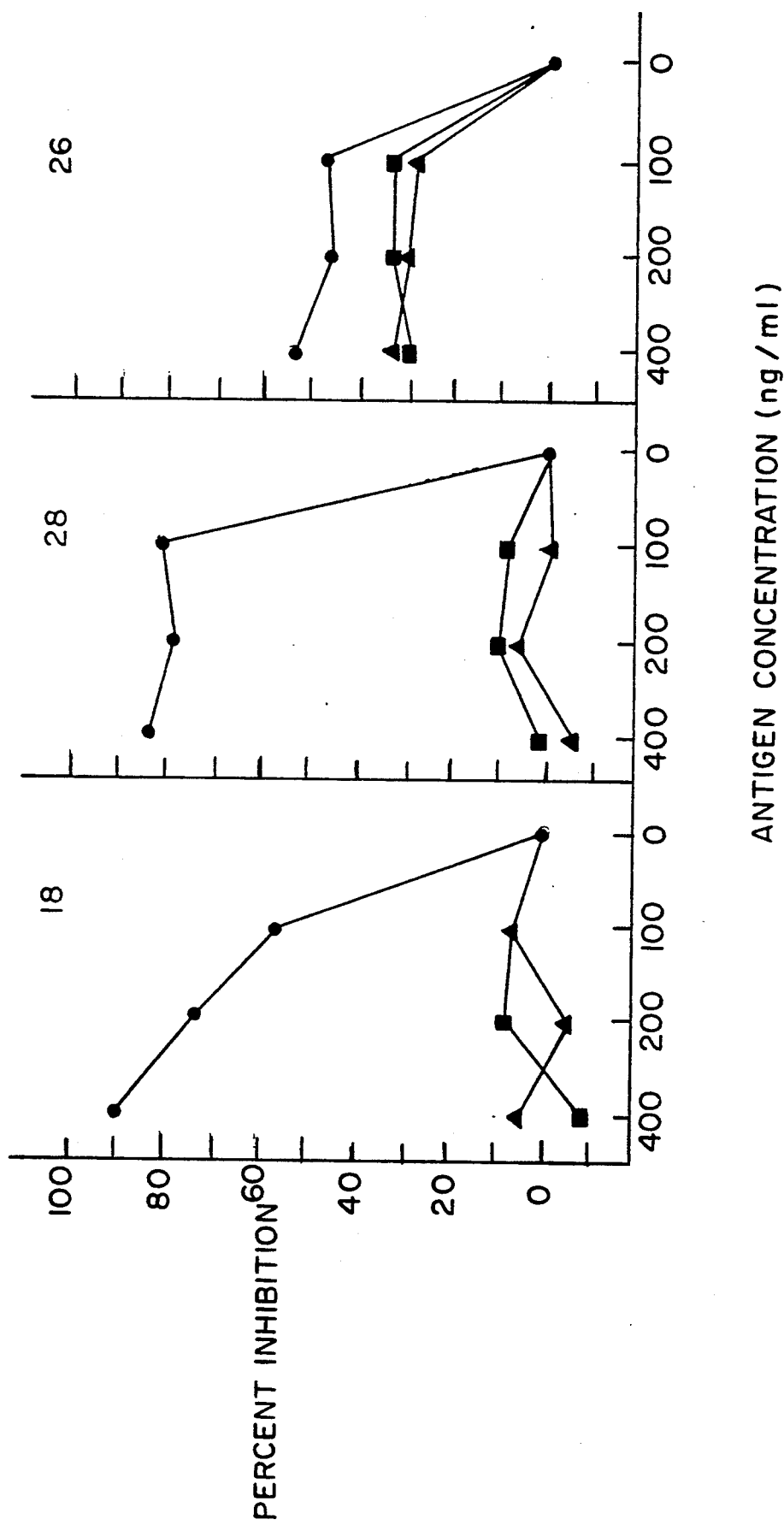
FIG. 3 shows percent inhibition curves of three human sera as determined by competitive ELISA. Binding curves represent antibody reactivity as tested on BDPDE-DNA with antigen competition; BDPDE-DNA O——O, $AFG_1$—DNA ♦——♦ control DNA ▲——▲.

Specificity of the antibodies or BPDE-DNA in the 11 positive sera was confirmed by the use of antigen competition ELISA. Examples of 3 of the antigen competition binding curves using BPDE-DNA, the 2,3-oxide of aflatoxin $B_1$ (AFB-DNA) as a control for modification of DNA by a chemical and unmodified DNA are shown in FIG. 3. The binding of antibodies from positive sera was inhibited specifically by BPDE-DNA for all of the positive samples; AFB-DNA and unmodified DNA had no significant effect except for serum #26. This pattern of inhibition for this serum shows that it contains antibodies to unmodified DNA as well as to BPDE-DNA.

The predominant immunoglobulin isotype of the anti-BPDE-DNA antibodies was determined to be IgG. Two of the 11 positive sera also contained BPDE-DNA reactive antibodies of the IgM class (cases 25 and 28). Antibody binding to BPDE-bovine serum albumin could not be detected suggesting that the antibodies present in the reactive sera recognize only BPDE as it is presented on DNA.

Cases with detectable levels of antibodies were compared to the other cases according to the number of years worked at the coke ovens. There was no statistically significant difference between the groups ($17.2 \pm 7.7$ years antibody positive vs. $18.1 \pm 8.0$ years, antibody negative). Three of the 11 cases with detectable antibodies were in jobs with highest exposure to benzene soluble particulates (27%) and 6 of the remaining 30 individuals (20%) were in these jobs at the time of the study.

These data clearly demonstrate that the presence of BPDE-DNA adducts and/or antibodies to the adducts are indicators of the exposure to BP or its carcinogenic metabolite and results from immune response to the BPDE-DNA adducts. Because all of the tested individuals have been exposed to substantial amounts of BP, the presence and varying titers of antibody in 28% of the cases may be more dependent on interindividual differences in metabolism of BP, DNA repair rates, and/or immune responsiveness to the adducts than variation in dose of BP. In those cases in which antibodies to BPDE-DNA adducts are detected, the time of the initial antigenic stimulus cannot be predicted, but considering the potential longevity of immunological memory that can be recalled by re-exposure to antigen, the initial antigenic stimulus could have occurred many years ago. Without being bound to any particular theory, it is proposed that antibodies to carcinogen-DNA adducts may be indicators of past exposure to specific environmental carcinogens and thus be significant in epidemiological indicators.

Without being bound to any specific explanation, it is postulated that the observatiopn that BPDE-DNA adducts were not found in every case probably reflects the variation in BP exposure and an individual's metabolic balance between activation and deactivation, and DNA repair capacity. Adduct levels may also be present in some subjects below the detection limit of the assays; in 11 cases tested by USERIA only small amounts of DNA were available for the assays. Compared to serum antibodies, the half-life of BPDE-DNA adducts may be considerably shorter. The persistence of antibody titers and adducts could be measured following cessation of exposure such as discontinuation of employment as a coke oven worker and/or of tobacco smoking. In animal studies, the persistence of BPDE-DNA adducts in vivo has been 1-2 weeks (Kulkarni, et al., *Cancer Res.* 441:97–101, 1984; Ashurst, et al., *Cancer Res.* 43:1024–1029, 1983). The precise contribution of the various sources of BP exposure, e.g., tobacco smoke, coke oven, and diet, to detachable levels of either adducts or antibodies to adducts remains to be studied.

The USERIA and SFS assay measure different endpoints and achieve their high sensitivity by different methods. USERIA utilizes antibodies to carcinogen-DNA adducts prepared by immunization of experimental animals with carcinogen-modified DNA and the immunological reaction is amplified in the solid-phase immunoassay by an immunoglobulin-conjugated enzyme that catalyzes a radioactive-labeled substrate to its products at a rapid rate, e.g., $10^5$ molecules per minute (Hsu, et al., supra; Harris, et al., supra). SFS measures a physical property of a carcinogen-DNA adduct, i.e., its fluorescence and PAHs, such as BP, are highly fluorescent. In contrast to the enzyme immunoassays in which the epitope recognized by the antibody may require a sterically intact carcinogen-DNA adduct, the level of detectability of a carcinogen in the fluorimetric assay can be increased by disruption of the adduct and removing the DNA which quenches the fluorescence of the carcinogen. For example, the level of detectability of BPDE in DNA can be increased 20- to 30-fold by hydrolysis to release the BP tetrols. Although the spectra of PAHs obtained from SFS are highly specific, it is possible that a similar spectrum can be produced from moities released by acid hydrolysis from non-BPDE chemicals that have adducted DNA. In addition, DNA adducts of non-BPDE chemicals may share the same epitope(s) recognized by the polyclonal rabbit antiserum to BPDE-DNA and cross-react in the USERIA. Although data obtained from a single type of assay may yield false positive results, positive results obtained by both SFS and USERIA are confirmatory of the presence of BPDE moiety in the DNA sample, and hence the existence of BPDE-DNA adducts.

In accordance with the present invention an assay kit is provided for detecting in human serum the presence of antibodies specific to any DNA-carcinogen adduct. The kit comprises in addition to those components commonly or routinely found in enzyme-linked-immunosorbent assay, such components or ingredients in containers as specific DNA adducts of those chemicals which are suspected of being carcinogenic; mammalian monoclonal or polyclonal antibodies against each of different DNA-carcinogen adducts, microtiter plate, micropipettes, microtiter reader, containers containing various reagents for the ELISA as described herein supra, instructions to carry out the assay and the like. Of course the kit can be designed for the detection of only a single DNA-carcinogen adduct or for a plurality of them as desired. Such a kit was not heretofore possible.

It is understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for detecting human exposure to genotoxic agents comprising:
    obtaining a sample of human serum;
    detecting the presence of antibodies specific to DNA-adducts of polycyclic aromatic hydrocarbons;
    correlating the presence of said antibodies to current or past exposure to genotoxic agents.

2. A method for detecting human exposure to genotoxic agents comprising:
    obtaining a sample of human serum;
    detecting the presence of antibodies specific to DNA-adducts of 7,12-dimethylbenzanthracene;
    correlating the presence of said antibodies to current or past exposure of genotoxic agents.

* * * * *